United States Patent [19]
Turk et al.

[11] Patent Number: 5,766,636
[45] Date of Patent: Jun. 16, 1998

[54] EDIBLE, LOW CALORIE COMPOSITIONS OF A CARRIER AND AN ACTIVE INGREDIENT AND METHODS FOR PREPARATION THEREOF

[75] Inventors: Richard S. Turk, East Lansing; Joel I. Dulebohn, Lansing; James W. Stitley, Jr., Tecumseh, all of Mich.

[73] Assignees: Natura, Inc.; Biotechnology Institute, Lansing, Mich.

[21] Appl. No.: 523,956

[22] Filed: Sep. 6, 1995

[51] Int. Cl.$^6$ ............................................. A61K 9/14
[52] U.S. Cl. ........................... 424/489; 424/488; 424/499
[58] Field of Search ........................... 424/489, 488, 424/490, 451, 499; 514/2

[56] References Cited

U.S. PATENT DOCUMENTS

| | | | |
|---|---|---|---|
| 4,283,219 | 8/1981 | Wagner et al. | 71/28 |
| 5,444,041 | 8/1995 | Owen et al. | 514/2 |
| 5,601,846 | 2/1997 | Milstein et al. | 424/499 |

OTHER PUBLICATIONS

J. A. Blair et al., Glass Technology, vol. 30, No. 5, pp. 190–191 (1989).
Levy et al., Photochem. Photobiol. A:Chem., 57 pp. 41–63, 1991.
Deis, Ronald, Food Technology, p. 94 (Dec. 1993).
J.M.V. Blanshard et al., The Glassy State of Foods, Nottingham University Press, pp. 207–222 (1993).
Richard S. Turk et al., Chemistry of Materials, 7 pp. 385–390 (1995).

*Primary Examiner*—Thurman K. Page
*Assistant Examiner*—William E. Bentston, Jr.
*Attorney, Agent, or Firm*—Quarles & Brady

[57] ABSTRACT

Edible, low calorie compositions contain, in addition to an active ingredient, such as flavoring agents, sweetening agents, therapeutic agents, cosmetic agents and luminescent agents, a gel or glass carrier which is the amorphous reaction product of a basic amino acid, a carboxylic acid, a source of metallic ions and water. Methods of making the compositions are disclosed.

4 Claims, No Drawings

EDIBLE, LOW CALORIE COMPOSITIONS OF A CARRIER AND AN ACTIVE INGREDIENT AND METHODS FOR PREPARATION THEREOF

FIELD OF THE INVENTION

The present invention generally relates to compositions of carriers and active ingredients. More particularly, it relates to edible, low calorie compositions of carriers and an active ingredient, such as a flavoring agent.

BACKGROUND OF THE INVENTION

Many active ingredients, such as flavoring agents and artificial sweeteners, because of their intensity or potency must be combined with carriers or bulking agents to obtain compositions having the desired concentration of the active ingredient for its intended use.

Currently available compositions of carriers and active ingredients have limitations. For example, it has not been possible to combine artificial sweeteners with known carriers to produce low calorie artificial sweetener compositions that possess all the desired organoleptic and physical properties of sugar. As a result, it has not been possible to make certain bakery products, such as low calorie cookies resembling crisp sugar cookies, or low calorie candies.

The replacement of sugar in foods is as difficult in practice as the replacement of fats. Bulking agents are added with the removal of fat or sugar, consequently replacing the total solids content in the food. Several types of bulking agents are used; maltodextrins, polyols and polydextroses. Maltodextrins are non-sweet nutritive polymers of glucose. They can be used as carriers of artificial sweeteners and to build soluble solids. They are added with other agents to inhibit sugar crystallization, control freezing point and increase viscosity of the food. They are fully caloric, (4 kcal/gm), ingredients. Polyols are bulking agents which include sorbitol, maltitol, xylitol, and lactitol. The general factors in using polyols are their caloric content, laxation potential, solubility, relative sweetness and stability. The average acceptable caloric value of polyols is 2.4 kcal/g. They are generally produced commercially by hydrogenation of sugars (glucose to sorbitol, fructose to mannitol, xylose to xylitol, lactose to lactitol) using metal catalysts.

Polydextroses are polymers of dextrose with a caloric content of about 1 kcal/g. Improvements in processing have produced cleaner tasting products. In various applications, polydextrose can also function as a humectant and a low calorie solids builder. They are used in baked goods, baking mixes, chewing gums, frostings, dressings, frozen dairy desserts, gelatins, fillings, hard and soft candies and puddings.

In baking, sucrose contributes to the flavor and tenderness of the baked item and controls the viscosity of the batter. Sugar also helps to limit the amount of free water which during baking determines the starch gelatinization temperature and the egg protein denaturation temperature. These temperatures are important to the final quality of the product. Flour provides starch which must gelatinize during baking by absorbing water resulting in increasing the viscosity and eventually solidifies as a gel when cooled. Polydextrose has been used up to about 30% for replacement of dextrose in cakes.

The state diagram of the system sucrose-water can be used to discuss structure-function relations in food systems. Plots of percent weight of sucrose in water versus glass and melting transition points of solid and solutions in the high sugar solids region (>60%) are relevant to low moisture food systems such as cookie, cracker and candy manufacture. The glass forming versus crystallizing behavior of sucrose represents a critical functional attribute of sugar in foods. The sucrose concentration in the food increases at baking temperatures until baking is complete and the food begins to cool. During cooling the food goes through a rubbery phase. At this point the food temperature lies within the glass transition temperature of the sucrose solution and the point of supersaturation of sugar in water. During cooling this sucrose can either be recrystallized or remain in the amorphous state.

In cookies, the sucrose (added in the recipe) and final water content are important. For example a cookie made with only 42 parts sucrose instead of 60 parts and baked to 4.5% moisture is a deformable rubber at room temperature as opposed to a desirable crisp glass. Also since room temperature is well above the glass transition temperature, diffusion processes are accelerated and degradation of the texture occurs.

Amorphous sugars in food are very stable below the glass transition temperature since physical processes occurring in the glass state are very slow. Physical changes in the amorphous state which are diffusion dependent include crystallization, stickiness, and collapse (time dependent loss of structure) and volatilization of flavors. Chemical changes in the amorphous state which are diffusion dependent include oxidation and off-flavor development.

There is a need for novel edible, low calorie compositions of carriers and active ingredients which do not have the limitations of the currently available compositions.

SUMMARY OF THE INVENTION

It is an object of the present invention to disclose novel edible, low calorie compositions of carriers and active ingredient(s).

It also is an object to disclose methods of preparing such novel compositions.

The novel compositions of the present invention are gels and glasses, which contain an active ingredient and a carrier which is the amorphous reaction product of a basic amino acid, a carboxylic acid, a metallic oxide or salt and water.

The term "gel" as used herein means aqueous compositions having high viscosity and rubber-like properties similar to concentrated sugar solutions, such as KARO® syrup. The term "gel" is not intended to denote any polymerization or crosslinking of the components of the aqueous composition.

The novel gel compositions of the present invention may be prepared by either adding the active ingredient to the carrier ingredients and forming a gel, or by forming a gel from the carrier ingredients and adding the active ingredient to the gel.

Novel glass compositions of the present invention can be prepared by dehydrating gel compositions containing active ingredient(s). If a granular composition is desired, the glass can be ground and sieved. Alternatively, a granular composition can be obtained by dehydrating a gel carrier to form a glass, grinding the glass to the desired size particles and blending the ground glass particles with the active ingredient to obtain a uniform, granular composition.

PREFERRED EMBODIMENTS OF THE INVENTION

In an especially preferred embodiment of the invention, a gel composition is prepared by dissolving an amino acid, lysine monohydrate, in water at about 60° C. to about 95° C. to form a concentrated solution, and adding to the solution a carboxylic acid, citric acid, a metallic oxide, magnesium oxide, and an active ingredient, an artificial sweetener, sodium saccharin. Upon standing at ambient temperature the gel composition forms immediately to within about 30 seconds.

The gel compositions at 65%–85% solids content show high viscosity (500 to 10,000 centipoise) behavior similar to concentrated sugar syrups and there is no problem with recrystallization as with sugar and other sugar substitutes. At even higher solids concentrations the gel compositions have the properties of a toffee or chewy candy without crystallization.

In another preferred embodiment, a glass composition is prepared by dehydrating a gel composition of the present invention by heating it in a microwave and then cooling it to form the glass. If desired, the glass can be ground to the desired particle size.

Representative of the basic amino acids which can be used to make the carriers of the present invention are the free base, salts and hydrates of lysine, ornithine, diaminopimelic acid, and amino acids of the formula: $NH_2(CH_2)_nCOOH$ in which n is 1 to 6, such as glycine, β-alanine, 4-aminobutyric acid, 5-aminovaleric acid, 6-aminocaproic acid and 7-aminoheptanoic acid. Some of these amino acids are available as food or pharmaceutical grade ingredients.

Representative of the carboxylic acids that can be used to make the carriers of the present invention are mono-, di-, and tri-carboxylic acids, such as acetic, citric, malic, succinic, tartaric, and fumaric acid.

The preferred metal oxide for use in preparing the carriers of the present invention is magnesium oxide, which is commonly used in foods. Other non-toxic metal oxides, such as zinc oxide and calcium oxide, or metal hydroxides, such as the hydroxides of magnesium, calcium, sodium, and potassium also can be used. In addition, soluble salts and carbonates of magnesium and calcium can also be used.

For the gel carrier the ratio of the basic amino acid to the carboxylic acid to the metallic ion source to the water is usually from ½ mole amino acid:1 mole carboxylic acid:½ mole metallic ion source:2 moles water to 2 moles amino acid:1 mole carboxylic acid:2 moles metallic ion source:10 moles water. In the preferred method of preparing the gel carrier, the amino acid is first dissolved in the water and the other ingredients are added to the amino acid solution to obtain a reaction mixture having a pH of about 5 to about 9. The ingredients are allowed to react at temperatures of from about 60° C. to about 95° C. The reaction mixture usually forms a gel within about 30 seconds.

The glass carrier is readily prepared from a viscous gel by dehydrating it under microwave radiation at a setting of 50% power to 100% power for about 0.5 minutes to about 15 minutes or by conventional oven drying methods at temperatures of about 120° C. to about 180° C. for about 10 minutes to about 60 minutes. The advantage of microwave drying is the rapid release of water and the development of the glass structure in the microwave.

The active ingredients that can be used with the carriers to form the compositions of the present invention include without limitation, flavoring agents, colors, cosmetic agents, luminescents and therapeutic agents. The only limitation on the active ingredient is that it is not adversely affected by the ingredients of the carrier.

A wide variety of therapeutic agents can be used as the active ingredient(s). Certain of the therapeutic agents also have fluorescent and phosphorescent properties including salicylic acid, p-amino benzoic acid, folic acid, vitamin A, fluorescein, riboflavin and pH indicators. The fluorescent and phosphorescent properties can be used in food products and the like to determine the viable life of the products and whether they have been exposed to adverse conditions.

Many flavorings are esters, acids and aldehydes which are potentially compatible with the components of the amino acid gel and glass. These flavorings or artificial flavors can be incorporated with artificial sweeteners to give a sugar candy, syrup or gum. One potential application is the introduction of flavor packets for coffee and tea products. A line of gummy bear-like products of different flavors for novelty uses is possible (e.g. edible gummy labels like glue or a glue stick/flavor).

A wide variety of flavoring agents can be used in the compositions of the present convention. Many flavorings are water insoluble or only slightly soluble in water. These flavorings such as cherry, mint, cinnamon, and orange are usually dissolved in a vegetable oil carrier. The oil can be added to the viscous gel of the present invention and uniformly suspended as small droplets of oil in the aqueous gel. When the gel carrier is dried these oil droplets become entrapped or encapsulated in the glass carrier. This entrapment can be seen under a light microscope as small oil globules immobilized in a clear glass.

The glass carrier provides a stable environment for the flavoring or fragrance and provides a means of controlled release. The advantage of the use of these carriers is that diffusion of volatile components from the oil droplet and through the glass carrier is extremely slow. However, full flavor or fragrance is released when the glass carrier is dissolved by mouth saliva or if the material is heated substantially above its glass transition temperature (130° C.).

Most flavorings also are susceptible to oxidation and entrapment is used to increase the shelf life. Prior art methods use spray drying of the flavor with polymeric gums which entrap the flavor. The method of the present invention differs from existing methods of entrapment since the flavoring is encased in the glass carrier. The carrier compositions containing flavoring agents can be used in cake mixes, beverage powders, gelatin desserts, candies, and the like.

Several classes of flavors with different organoleptic properties and typical flavoring agents are listed below:

| Flavoring | Chemical Name |
| --- | --- |
| Balsamic | |
| Anise | methyl p-anisate |
| Balsam | cinnamyl alcohol |
| Caramel | acetanisole |
| Chocolate | maltol, 2 methyl butyraldehyde |
| Cinnamon | cinnamaldehyde |
| Honey | allyl phenylacetate |
| Sweet | ethyl vanillin |
| Vanilla | vanillin |
| Citrus | |
| Lemon | citral dimethyl acetal |
| Lime | undecyl alcohol |
| Orange | decyl acetate |
| Coffee | |
| Coffee | methyl cyclopentenolone |
| Fatty | |

-continued

| Flavoring | Chemical Name |
| --- | --- |
| Butter | 2,3 pentanedione |
| Cheese | butyric acid |
| Creamy | tributyrin |
| Floral | |
| Blossom | neryl acetate |
| Carnation | 5-phenyl 1-pentanol |
| Gardenia | geranyl tiglate |
| Hyacinth | p-tolyl phenylacetate |
| Jasmin | benzyl acetate |
| Lilac | terpineol |
| Rose | butyl phenylacetate |
| Fruity | |
| Apple | isoamyl hexanoate |
| Apricot | allyl butrate |
| Banana | allyl heptanoate |
| Cherry | benzyl acetate |
| Coconut | decalactone |
| Grape | isobutyl isobuyrate |
| Melon | 2,6 dimethyl 5-heptenal |
| Peach | decalactone |
| Pear | ethyl decanoate |
| Pineapple | hexyl butyrate |
| Plum | 2-hexenal |
| Raspberry | butyl valerate |
| Strawberry | ethyl isobutyrate |
| Minty | |
| Minty | dl-menthol |
| Nutty | |
| Almond | benzaldehyde |
| Hazelnut | 2,3 diethylpyrazine |
| Peanut | 2-methoxy 3 methylpyrazine |
| Walnut | 2,3 dimethylpyrazine |
| Smoky | |
| Smoky | guaiacol |
| Woody | cuminaldehyde |

The practice of the present invention is further illustrated by the examples.

EXAMPLE 1

Preparation of Gel and Glass

A gel was prepared by dissolving 175 gm of lysine monohydrate in 105 gm water at 60° C.–95° C. To this solution was added 43 gm MgO, 205 gm of citric acid (anhydrous). The gel that formed after about 10 seconds was microwaved at 100% power (1400 watts/2450 megahertz) for 7 to 10 minutes and then cooled in a freezer to room temperature (20° C.) to form a glass. The glass was ground and sieved to give various particle sizes similar to table sugar. The following mixture of mesh sizes was prepared: 24 Mesh (33%), 32 Mesh (41%), 42 Mesh (17%) and 60 Mesh (6%).

The glass contained 29 gm (1 ounce), 11.7 gms by weight protein, 0% carbohydrate, 0% fat, no cholesterol and no sodium. The mineral content was 1300 mg magnesium and 480 mg calcium. The calorie content was 71.6 kilocalories or 2.46 kcal/gm.

EXAMPLE 2

Preparation of Gel and Glass

The procedure of Example 1 was followed except that the amount of magnesium oxide in the formulation was reduced. The gel was formed by dissolving 132 gm of lysine monohydrate in 150 gm water at 60° C.–95° C. To this solution were added 21.6 gm MgO and 6.72 gm CaO and 147 gm of citric acid (monohydrate). The resulting gel was microwaved at 100% power (1400 watts/2450 megahertz) for 7–10 minutes and then cooled to 20° C. in a freezer to form a glass. Because calcium citrate is only slightly soluble in water the ratio and amount of CaO/MgO should be controlled to produce a clear gel and glass. Typical ratios range from 0 to 0.33.

EXAMPLE 3

Preparation of Sugar Substitute

About 250 gms of the ground glass carrier of Example 1 was mixed with 6.3 gm of aspartame to form a granular, sugar-like, artificial sweetener. The carrier-aspartame composition was used to replace 250 g of sugar in the following recipe for sugar cookies.

500 g flour
250 g sugar or sugar replacer
225 g shortening
25 g nonfat dry milk
5 g salt
4 g sodium bicarbonate
5 g baking powder
85 g water The batter was baked at 350° F. for 10 minutes. The batter and cookies had the same color and appearance of control sugar cookies made using sugar. The amount of citrus flavor of the cookies depended on the amount of anhydrous citric acid used. Cookies made with the ground glass carrier of Example 1, which was made with anhydrous citric acid, had a lemon taste. Similar cookies made with a ground glass carrier, which was made with an equal amount of citric acid monohydrate in place of the anhydrous citric acid, did not have a lemon or citrus flavor.

EXAMPLE 4

Preparation of Sugar Substitutes

Artificial sweeteners that can be used with the carriers of the present invention to replace sugar besides aspartame, include acesulfame K, and sodium saccharin.

Artificial sweetener compositions may be prepared as follows:

To 240 gm of the ground glass mixtures from Examples 1 and 2 are added the following amounts of the artificial sweeteners: 1.2 gm of acesulfame or 0.4 gm of sodium saccharin. The ground glass and artificial sweetener mixtures had a tart/sweet taste using the ground glass of Example 1 or a sweet taste using the ground glass mixture of Example 2.

EXAMPLE 5

Alternative Method of Preparing Sugar Substitute

A gel was prepared by dissolving 100 gm of lysine monohydrate in 100 gm water at 60° C.–95° C. To this solution was added 24 gm MgO and 115 gm of citric acid (anhydrous) and 1.195 gm acesulfame K. The gel which formed after 10 seconds was microwaved at 100% power (1400 watts/2450 megahertz) for 7 to 10 minutes and then cooled in a freezer to 20° C. to form a glass. The glass was ground and sieved to give various particle sizes similar to table sugar. The following mixture of mesh sizes was prepared: 24 Mesh (33%), 32 Mesh (41%), 42 Mesh (17%)

and 60 Mesh (6%). The material had the organoleptic and physical properties of crystalline table sugar.

EXAMPLE 6

Preparation of Sugar Substitute with Calcium Oxide

A gel was formed by dissolving 110 gm of lysine monohydrate in 100 gm water at 60° C.–95° C. To this solution was added 18 gm MgO and 5.6 gm CaO and 122.5 gm of citric acid (monohydrate) and 1.243 gm acesulfame K. The gel that formed after 20 seconds was microwaved at 100% power (1400 watts/2450 megahertz) for 7 to 10 minutes and then cooled to 20° C. in a freezer to form a glass. The material when ground as described in Example 5 had the desired properties of crystalline sugar and a clean sweet taste without a sour aftertaste.

Additional sugar substitutes were made using 6.402 gms of encapsulated aspartame (Nutrasweet) or 2.502 gms of powdered aspartame in place of the acesulfame K.

EXAMPLE 7

Preparation of Sugar Substitute with Malic Acid

A clear gel was made by adding 50 gm of lysine monohydrate and 50 gm of lysine monohydrochloride to 100 gm of water at 60° C.–95° C. To this solution were added 20 gm MgO and 82 gm of malic acid and 60 ml of sodium saccharin. The slightly yellow gel which formed immediately was microwaved at 100% power (1400 watts/2450 megahertz) for 5 to 7 minutes and cooled to 20° C. The resulting glass which was ground as described in Example 5 had the sweet taste and the texture of crystalline sugar.

The pH of the glass can be reduced by increasing the ratio of the lysine HCl/lysine HOH from 1.0 to 2.5. Flavor changes from neutral/sweet to sour/sweet are obtained if the ratio is increased and other ingredients are kept constant.

The glasses of Examples 1–2 and 4–7 possess a blue fluorescence and a blue green phosphorescence lasting up to 20 seconds when excited by longwave UV light. As a result these glasses can be used to impart fluorescence or phosphorescence to the products to which they are added.

EXAMPLE 8

Preparation of Hard Candy

A hard candy was prepared without the use of sugar by heating 100 gm of water (60° C.–90° C.) and dissolving in it 110 gm lysine monohydrate. To this solution was added 18 gm MgO, 5.6 gm CaO and 122.5 gm of citric acid monohydrate. A clear gel formed after 10 seconds. The gel was cooled to just above room temperature and artificial sweetener (1.24 gm acesulfame K), food coloring (20 drops red) and flavoring (40 drops artificial cherry) were added. Equal portions of the gel were dehydrated by microwaving at 100% power (1400 watts/2450 megahertz) for 7 to 10 minutes or oven drying at 120° C. for 30 minutes.

The resulting glasses were brittle like sugar and had the taste and texture of a hard candy made from sugar.

EXAMPLE 9

Preparation of Hard Candy

The procedure of Example 8 was repeated reducing the relative amounts of magnesium oxide and calcium oxide by the addition of sodium hydroxide. To the lysine solution were added, in order, 6.1 gm NaOH, 12.5 gm MgO, 3.0 gm CaO and 122.5 gm of citric acid monohydrate to form a clear gel. The gel was cooled to just above room temperature and artificial sweetener (1.24 gm acesulfame K), food coloring (20 drops red) and flavoring (40 drops artificial cherry) are added. The gel was dehydrated by microwaving at 100% power (1400 watts/2450 megahertz) for 7 to 10 minutes or by oven drying at 120° C. for 45 minutes to obtain a glass which had the taste and texture of a hard candy.

EXAMPLE 10

Preparation of Taffy-like Product

A gel was prepared from 100 ml water, 110 gm lysine monohydrate, 18 gm MgO, 5.6 gm CaO, and 122.5 gm citric acid monohydrate (65% solids by weight). The mixture was evaporated to between 78 to 81% solids by weight after which flavoring and artificial sweetener 0.4 gms (sodium saccharin) were added. The candy was soft and chewy with the texture of taffy.

EXAMPLE 11

Preparation of Glass with PABA

A glass was prepared from 10 grams of lysine monohydrate dissolved in 6 gm water, 2.45 gm MgO, and 7.45 gm of succinic acid. Para aminobenzoic acid (PABA) was added at 0.01%–0.16% by weight of the total dry ingredients. The clear gel which formed was dried in a microwave at 100% power (1400 watts/2450 megahertz) for 60 seconds and cooled to 20° C. to form a glass. The phosphorescence of the material was observed to have different colors under short and long wavelength UV light. At 365 nm the phosphorescence was blue/green lasting up to 25 seconds and was similar to that observed without the PABA. Under shortwave UV (254 nm) the phosphorescence was intensely blue/white lasting up to 20 seconds. Without PABA the shortwave phosphorescence was substantially reduced in intensity and was less blue and more green in color. The fluorescence of the solid glass was substantially brighter than the gel at both wavelengths of excitation.

EXAMPLE 12

Preparation of Glasses with Chromophores

Compositions containing salicylic acid (ortho hydroxybenzoic acid, benzoic acid, and vanillin (3-methoxysalicylaldehyde)) was prepared by the method of Example 11 but with chromophores in place of the PABA. The following table shows the phosphorescence observed after excitation with UV light at 254 nm or 365 nm:

| Compound | Color/Intensity (254 nm) | Color/Intensity (365 nm) |
| --- | --- | --- |
| Salicylate | blue++ | blue++ |
| Benzoic | green– | blue/green– |
| vanillin | blue/white++ | blue/green– |
| PABA | blue/white++ | blue/green– |

(–indicates no change from control ++indicates intense color observed)

EXAMPLE 13

Preparation of Gels and Glasses with Other Amino Acids

Clear gel and glasses were prepared from other amino acids having a linear carbon chain separating the amino and carboxyl group. The following amino acids and (weights) were used as substitutes for lysine monohydrate in Example 11 above: glycine (4.6 gm), β-alanine (5.4 gm), 4-aminobutyric acid [GABA] (6.3 gm), 6-aminocaproic acid (7.9 gm). The presence of 0.0086 gm vanillic acid (0.06%) produced a green/blue phosphorescence. Without the vanillic acid there was no phosphorescence.

EXAMPLE 14

Preparation of Glass with Fluorescein

The method of Example 11 was repeated except that the PABA was replaced by adding 0.009 gm of fluorescein (sodium salt). The solid fluorescein salt did not fluoresce unless dissolved in a solvent. The dried glass showed a brilliant yellow/white fluorescence. The solid glass was placed in pure ethanol and it was observed that no fluorescein was dissolved from the glass over several months.

EXAMPLE 15

Preparation of Glass with Vitamin A

The method of Example 11 was repeated but 10 gm lysine and 10 ml water were used to dissolve 4 gm ZnO, 8.3 gm malic acid, and 0.01 gm of Vitamin A acetate. The yellow gel was microwaved to give a solid glass having Vitamin A activity and giving blue fluorescence (with longwave UV excitation) and green phosphorescence.

EXAMPLE 16

Preparation of Glass with Vitamin E

The method of Example 15 was repeated but 0.036 gm of Vitamin E was used instead of Vitamin A acetate.

EXAMPLE 17

Preparation of Glass with Folic Acid

The method of Example 15 was repeated but 0.02 gm folic acid was used in place of Vitamin A acetate.

EXAMPLE 18

Preparation of Glass with Glycine

Differences in phosphorescence were observed by substituting glycine for lysine. With Vitamin A acetate blue phosphorescence was observed if lysine was used but no phosphorescence was observed with glycine. Either 10 gm lysine or 4.7 gm glycine and 10 ml of water dissolve 2.45 gm MgO, 7.4 gm succinic acid and 0.02 gm Vitamin A acetate which is dried in a microwave.

EXAMPLE 19

Preparation of Glass with pH Sensitive Active Ingredient

Compounds which are sensitive to pH can be incorporated in the glass. 0.01 gms of bromophenol blue or bromocresol purple were dissolved in the lysine or glycine glass of Example 18. A red fluorescence was observed with the dry glasses. The red fluorescence corresponds to the emission observed with these dyes dissolved in ethanol. Excitation at 260 nm gives fluorescence at 585 nm for these dyes.

The products prepared as described in the Examples are low in calories. The calories supplied by the amino acid portion of the gel or glass can be treated as calories supplied by protein. In humans the protein fraction breaks down to $CO_2$, $H_2O$ and urea. The amount of protein breakdown can normally be measured by analysis of the urine and feces as well as measurement of respiratory gas exchange. The average metabolic energy (1 Cal=1 kilocalorie) derived from protein is 4.1 Cal/g, from carbohydrate, 4.1 Cal/g, and from lipid, 9.3 Cal/g. Since carbohydrate and lipid are not components of this food they are not included in the calculation. Normally however, the foodstuff containing the gel or glass may also contain carbohydrate, fat and other protein components and an alternative (indirect) approach is needed to calculate calories.

It also can be assumed that the organic acid portion is fully digested and the acids are fully metabolized to $CO_2$ and $H_2O$. It is reasonable to use heat of combustion data for these compounds. The inorganic components and water do not contribute calories to the diet. However, the calcium and magnesium in the material may act to prevent absorption of the components into the gut (laxative effect) and reduce the calorie intake.

It will be apparent to those skilled in the art that a wide variety of active ingredients may be incorporated into the compositions of the present invention without departing from the spirit and scope of the invention. Therefore, it is intended that the invention only be limited by the scope of the claims.

We claim:

1. A composition comprising a carrier and an active ingredient, said carrier comprising the amorphous reaction product of a basic amino acid, a carboxylic acid, a metallic ion selected from the group consisting of magnesium, sodium, calcium, potassium and zinc ions and water, said amorphous reaction product being selected from the group consisting of a gel or glass.

2. A composition of claim 1 in which the active ingredient is selected from the group consisting of an oil soluble material, a flavoring agent, a therapeutic agent and an artificial sweetener.

3. A composition of claim 1 in which the glass is ground into particles.

4. A sugar substitute comprising a carrier which is the amorphous reaction product of a basic amino acid, a carboxylic acid, a metallic ion selected from the group consisting of magnesium, sodium, calcium, potassium and zinc ions and water in combination with an artificial sweetener, said amorphous reaction product being selected from the group consisting of a gel or glass.

* * * * *